United States Patent

Nagels et al.

[11] Patent Number: 5,702,945
[45] Date of Patent: Dec. 30, 1997

[54] CULTURE VESSEL FOR CELL CULTURES ON A CARRIER

[75] Inventors: Hans-Otto Nagels, Bovenden; Dieter Schröder, Osterode; Eckart Kopowski, Braunschweig, all of Germany

[73] Assignee: Heraeus Instruments GmbH, Hanau, Germany

[21] Appl. No.: 595,351

[22] Filed: Feb. 1, 1996

[30] Foreign Application Priority Data

Feb. 15, 1995 [DE] Germany .................. 195 04 958.6

[51] Int. Cl.$^6$ ........................................... C12M 3/06
[52] U.S. Cl. ............................ 435/297.1; 435/297.5; 435/299.1; 435/299.2
[58] Field of Search ....................... 435/180, 182, 435/240.23, 240.24, 240.241, 240.242, 240.243, 297.1, 297.2, 297.4, 297.5, 299.1, 305.1, 299.2, 305.2, 305.3, 305.4, 394, 395, 398, 389, 401, 402

[56] References Cited

U.S. PATENT DOCUMENTS

| | | | |
|---|---|---|---|
| 3,223,595 | 12/1965 | Brewer | 195/139 |
| 4,661,455 | 4/1987 | Hubbard | 435/240 |
| 4,661,458 | 4/1987 | Berry et al. | 435/284 |
| 4,717,668 | 1/1988 | Keilman et al. | 435/296 |
| 4,748,124 | 5/1988 | Vogler | 435/240.241 |
| 4,959,322 | 9/1990 | Sakai | 435/311 |
| 4,978,616 | 12/1990 | Dean, Jr. | 435/70.3 |
| 4,988,623 | 1/1991 | Schwarz et al. | 435/286 |
| 5,026,650 | 6/1991 | Schwarz et al. | 435/286 |
| 5,110,741 | 5/1992 | Ohi et al. | 435/284 |
| 5,153,131 | 10/1992 | Wolf et al. | 435/240.24 |
| 5,155,034 | 10/1992 | Wolf et al. | 435/240.24 |
| 5,155,035 | 10/1992 | Schwarz et al. | 435/240.24 |
| 5,288,631 | 2/1994 | Baumgartner et al. | 435/240.242 |
| 5,449,617 | 9/1995 | Falkenberg et al. | 435/240.25 |

FOREIGN PATENT DOCUMENTS

| | | | |
|---|---|---|---|
| 0 180 165 | 5/1986 | European Pat. Off. | |
| 286688 B1 | 2/1993 | European Pat. Off. | |
| 4-332561 | 11/1992 | Japan | 435/299.1 |
| 2178447 | 2/1987 | United Kingdom | 435/299.1 |
| WO 90/05179 | 5/1990 | WIPO | |
| 90/15877 | 12/1990 | WIPO | 435/297.2 |
| WO 91/02555 | 3/1991 | WIPO | |

OTHER PUBLICATIONS

*In Vivo Toxicology*, A Journal of Molecular and Cellular Toxicology, vol. 7, No. 2, Summer, 1994.

(List continued on next page.)

*Primary Examiner*—William H. Beisner
*Attorney, Agent, or Firm*—Workman, Nydegger & Seeley

[57] ABSTRACT

The purpose of the present invention is to attain optimal gas exchange, nutrient supply and disposal of metabolic waste products without contamination during high-density cell cultivation of adherent cells. The culture vessel of the present invention provides methods and apparatus for the cultivation of cells on a three-dimensional carrier in a closed cell culture chamber, the supply with oxygen taking place across a gas-permeable gas exchange membrane bordering the cell culture chamber and the supply with nutrients taking place across a dialysis membrane bordering the cell culture chamber, across which nutrients are transported and across which metabolic products are removed, without the danger of contaminating the cells during contact with the tools necessary for manually separating the cells being cultivated from the nutrient medium. The cell culture chamber of the present invention features a vessel that is impermeable to fluids on all sides except for the boundary formed by the dialysis membrane. This makes it possible to move the cell culture intensively within a fluid nutrient supply medium. It is neither necessary to open the cell culture chamber during cultivation to introduce new nutrients, nor is it necessary for the design to include components which reach into the cell culture chamber, and form an additional source of contamination. The gas exchange membrane is detachable to allow removal of the cultivated cells in a uniform layer on the carrier, and the carrier is bio-degradable to eliminate the need to remove the cells from the carrier prior to use, such as in the transplantation of skin for example.

16 Claims, 4 Drawing Sheets

OTHER PUBLICATIONS

*NASA Tech Briefs Inventors of the Year, Johnson Team's Biotech Breakthrough*, Mar. 1992, vol. 16, No. 3.

*Medical Research System*, pp. 56–57, Spinoff, 1993, NASA Publication.

Weichert, et al., *In Vitro Production of Monoclonal Antibodies in High Concentration in a New and Easy to Handle Modular Minifermenter*, Proceedings of the "World Congress on Alternatives an Animal Use in the Life Sciences," Nov. 14–19, 1993, Baltimore, MD/USA.

Falkenburg, et al., *A Simple and Inexpensive High Density Dialysis Tubing Cell Culture System for the In Vitro Production of Monoclonal Antibodies in High Concentration*, Journal of Immunological Methods, 165 (1993) 193–206.

1992 Fisher Product Catalog, p. 16.

Lewis, Marian L., et al., *Use of Microgravity Bioreators for Development of an In Vitro Rat Salivary Gland Cell Culture Model*, Journal of Cellular Biochemistry 51, pp. 265–273 (1993).

Spaulding, et al., *Viewpoint, Advances in Cellular Constuction*, Journal of Cellular Biochemistry, (Mar. 1993), vol. 51, pp. 249–251.

Stephens, T., *NASA Allies Tour Biomedical Spinoffs*, The Journal of NIH Research, (Dec. 1991) vol. 3, pp. 28–31.

Beardsley, T., *Shear Bliss, A Bioreator Grows Cell That Resemble Real Tissue*, Scientific American, (Feb. 1992) p. 27.

CULTURE VESSEL FOR CELL CULTURES ON A CARRIER

BACKGROUND OF THE INVENTION

1. Related Applications

A claim for priority of German Patent Application, 195 04 958.6, filed Feb. 15, 1995, incorporated herein by reference, is made for this application.

2. The Relevant Technology

The present invention concerns a culture vessel for cell cultures on a carrier with the cell culture being accommodated on a three-dimensional carrier in a culture vessel, and with a supply chamber which provides the cell culture with nutrients and oxygen across a dialysis membrane, which separates the supply chamber from the culture chamber and allows for metabolic wastes to be transported away from the cell culture into the supply chamber, and with a detachable gas exchange membrane which is permeable to gas and allows for ease of access to the cell culture, and forms the outside border of the culture chamber.

Cell culture vessels with carriers are used for the cultivation of so-called adherent cells. These cells multiply only on a solid substratum as opposed to cells, such as hybridomas, that grow suspended in cell culture media. Therefore the cultivation of adherent cells requires that a suitable carrier be available. The adherent cells usually grow on the carrier in a monolayer. In addition, it has been shown that some types of adherent cells need a three-dimensional carrier body for optimal growth.

European Patent B1 286 688 describes a technique for the cultivation of adherent cells and a carrier suitable for that purpose. It proposes a carrier in the form of a fabric made of ultrafine fibers. For example, the fabric is weft knitted, warp knitted, or woven. For cell cultivation the familiar carrier is sterilized and then placed together with a nutrient solution in a plastic Petri dish. This assembly is then treated in an incubator under a suitable atmosphere.

The porosity of the familiar carrier ensures optimal cell growth, a good supply of nutrients, and especially oxygen, to the cells, and the removal of contaminants. But it has been shown that the attainable cell density is not adequate for many applications. To attain higher cell densities on the carrier it is necessary to exchange the nutrient medium from time to time. To do this the cells being cultivated must be separated from the nutrient medium, which is a costly procedure. Furthermore, the danger of contaminating the cells during contact with the necessary tools and during the cultivation in the incubator is especially problematic in the familiar technique and arrangement.

SUMMARY AND OBJECTS OF THE INVENTION

An object of the present invention is to provide methods and apparatus permitting ample and uniform gas and nutrient exchange within a cell culture vessel such that cultivation of high cell densities is achieved utilizing a carrier in a closed cell culture chamber, the oxygen being supplied across a gas-permeable gas exchange membrane bordering the cell culture chamber on one end, and the nutrients being supplied across a dialysis membrane bordering the cell culture chamber on the other end, through which nutrients are transported and metabolic products are removed, without the danger of contaminating the cells during contact with the tools necessary for manually separating the cells being cultivated from the nutrient medium.

Another object of the invention is to provide methods and apparatus permitting the removal of the cultivated cells from the cell culture chamber, the gas exchange membrane being detachable to allow the cultivated cells to remain in a uniform layer on the carrier, and the carrier being biodegradable to eliminate the need to remove the cells from the carrier prior to use, such as in the transplantation of skin for example.

To achieve the foregoing objects, the cell culture chamber of the present invention features a vessel that it is impermeable to fluids on all sides except for the boundary formed by the dialysis membrane. This makes it possible to move the cell culture intensively within a fluid nutrient supply medium. The rotation ensures a uniform supply of nutrients and oxygen to the cell culture on the carrier.

At the same time the closed form of the cell culture chamber prevents the introduction of cytotoxins. When the supply chamber is impermeable to fluids, except for its peripheral surface which is formed by the dialysis membrane, this prevents contamination of the supply medium during cultivation. The cell culture chamber and the supply chamber can be solidly connected with one another. It is neither necessary to open the cell culture chamber during cultivation to introduce new nutrients, nor is it necessary for the design to include components which reach into the cell culture chamber, and form an additional source of contamination.

The total surface area, the material, and the thickness of the gas exchange membrane ensure that the oxygen supply covers the oxygen demand of the high density cell culture. The cell culture vessel of the present invention features a gas-permeable gas exchange membrane which is made so that it can be separated from the cell culture chamber. This makes it possible to open the cell culture chamber by removing the gas exchange membrane and to remove the carrier which is covered with cells after the end of cell cultivation. It has proven worthwhile to provide the gas exchange membrane with a removal device.

The cell culture vessel of the present invention features a carrier placed in a closable cell culture chamber. Any three-dimensional body on which cells can multiply is suitable as a carrier. It has proven especially worthwhile to use a three-dimensional network of fibers or fiber fragments. Such a network is distinguished by a large surface-to-volume ratio and allows the cultivation of high cell densities. The surface of the network can be structured or chemically modified in such a way to promote the adhesion of the cells to be cultivated. The fibers can be either solid or hollow. If the fibers are hollow an additional surface is available for the cells. The network can be inserted into the cell culture chamber, for example in the form of a matte.

A carrier which is built of several layers which can be separated from one another has proven especially advantageous. Such a carrier makes it possible, after the cell cultivation has finished, to remove individual layers each of which is coated with the cell culture. These layers can be coated with skin cells and can be used, for example, as a skin replacement during transplantations. A special advantage of such a carrier also consists of the fact that a single cell culture can produce a large skin replacement surface simultaneously. In this connection a carrier which consists of a material which can be broken down biologically has proven especially worthwhile.

The present invention also features a carrier held on a support piece. This allows the carrier itself to have very thin walls because the mechanical stability is taken over by the support piece.

These and other objects and features of the present invention will become more fully apparent from the following description and claims, or may be learned by the practice of the invention as set forth hereinafter.

BRIEF DESCRIPTION OF THE DRAWINGS

Examples of embodiments of the invention are presented in the drawing and are explained in more detail below. The drawings show, in particular.

DETAILED DESCRIPTION OF THE PREFERRED EMBODIMENTS

Figure 1:
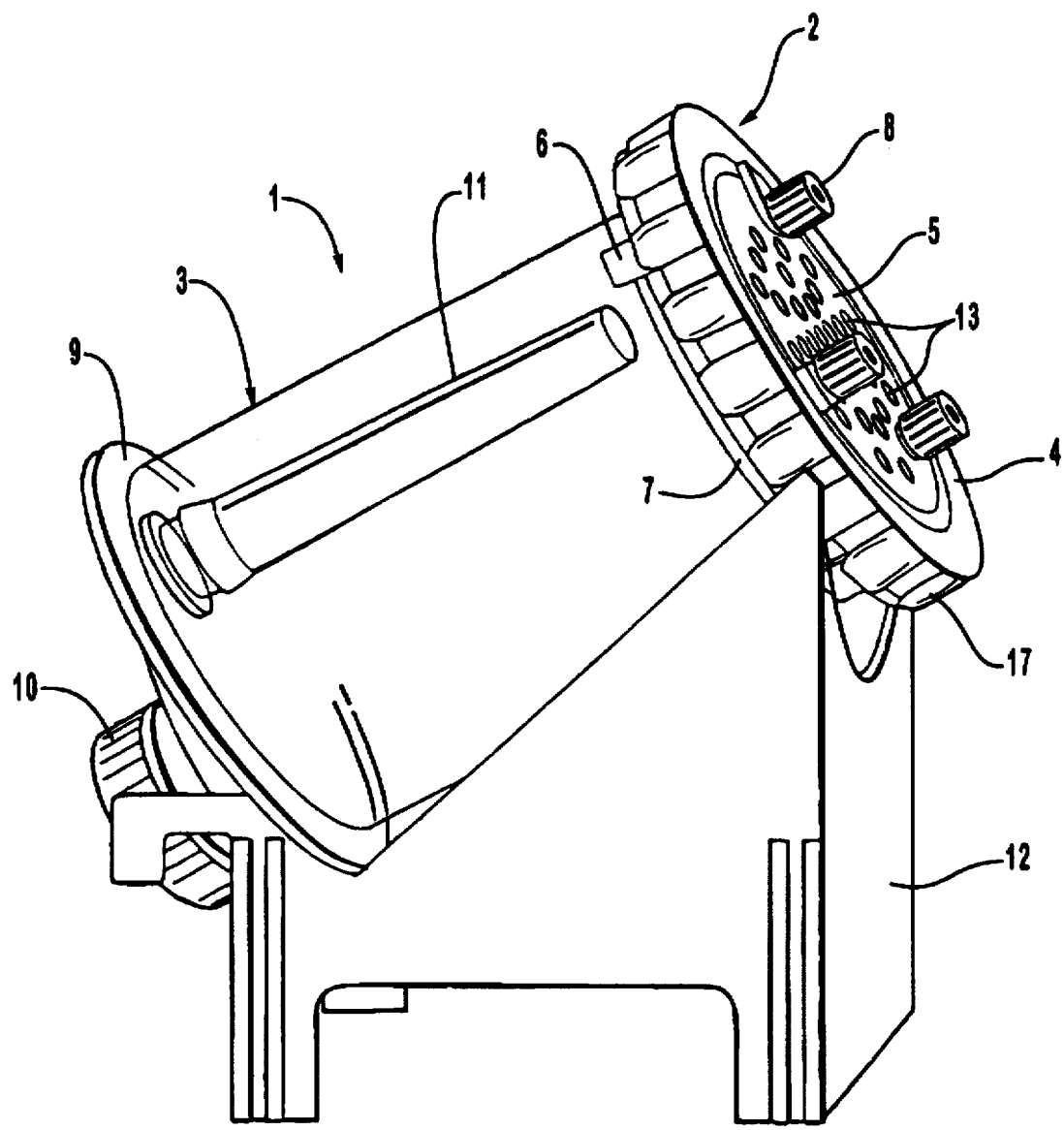
FIG. 1 a side view of a culture vessel for cell cultures with a carrier according to the invention which is placed on a stand.

In FIG. 1, the reference number 1 refers to a culture vessel, in accordance with the invention, in its entirety. The culture vessel may conveniently be placed on a stand 12 when desired. The culture vessel 1, which is essentially cylindrical in shape, is constructed in a modular fashion and is composed of a production module 2 and a supply module 3. The production module 2 is in the form of a circular ring 4 which is approximately 1 cm high, and preferably made from stable plastic. The outward-facing side of the circular ring is covered by a gas exchange membrane 5, and the inward-facing side of the circular ring, which faces the supply module 3 is covered by a dialysis membrane 18 (shown in FIG. 2). In order to hold the production module 2 to the supply module 3, a circular ring 4 is provided with catch hooks 6 that snap over an annular ring 7 which runs around the circumference of the upper edge of the supply module 3. When snapped in, the production module 2 faces the supply module 3. A sealing ring (not shown) placed between the faces ensures that the connection between production module 2 and supply module 3 is sealed to gases and fluids.

The production module 2 is filled with a cell suspension through one of the three openings 25 (shown in FIGS. 3 and 4), preferably having Luer lock connections, which can be closed using caps 8 so that they are sealed to gases and fluids. In order to fill the supply module 3 with nutrient solution for the cells to be cultivated, it is provided with a filling aperture which can be closed with a screw cap 10.

As a result of the preferred configuration illustrated in FIG. 1, the cell culture chamber can be made closable so that it is impermeable to fluids on all sides except for the boundary formed by the dialysis membrane. This makes it possible to move the cell culture intensively within a fluid nutrient supply medium, for example to rock it or to roll it. The intensive motion allows the cell culture both a good supply of nutrients and oxygen and also rapid removal of contaminants. It has proven to be especially favorable in practice to rotate the culture vessel 1 during cultivation. The rotation ensures a uniform supply of nutrients and oxygen to the cell culture on the carrier.

An additional advantage of the preferred embodiment illustrated in FIG. 1 is the prevention of contamination of the supply medium during cultivation. Because the cell culture chamber and the supply chamber can be solidly connected with one another, the closed form of the cell culture chamber prevents the introduction of cytotoxins. The cells are continuously supplied with nutrients from the supply chamber across the semi-permeable dialysis membrane, while catabolic and metabolic products are likewise continuously removed across the dialysis membrane out into the supply chamber. The dialysis membrane prevents uncontrolled distribution of the cells in the supply medium and restricts the cell culture within the cell culture chamber. Therefore it is not necessary to separate the cell culture from the medium when the supply medium is exchanged.

Gas is likewise continuously supplied to the cells across the dialysis membrane and additionally across the gas exchange membrane. Therefore it is neither necessary to open the cell culture chamber during cultivation to introduce new nutrients, nor is it necessary for the design to include components which reach into the cell culture chamber, such as hoses, pipes, or rotary transmission leadthroughs to supply gas to the cells. Such components form an additional source of contamination.

FIG. 1 shows the lower edge of the supply module 3 which is provided with a rolling edge 9 that runs around the circumference and projects past the cylindrical surface of the supply module 3. When the culture vessel 1 is rolled around its longitudinal axis it rests only on its rolling edge 9 and circular ring 4; thus no stress is placed on the cylindrical surface of the supply module.

One embodiment of the cell culture vessel which has proved itself to be especially advantageous is shaped like a kind of cylindrical bottle which can roll around an axis of rotation. It is advantageous if the cell culture chamber and the supply chamber are connected solidly with one another but can be separated. The nutrient medium is thus provided in a supply chamber adjacent to the cell culture chamber, which is impermeable to fluids, except for its peripheral surfaces which are formed by the dialysis membrane. Necessary openings, for example in the form of partitions, to remove nutrient medium or samples of the cell culture, are therefore designed so that they can close. The rolling motion thoroughly mixes the nutrient medium inside and outside the cell culture chamber and therefore supplies the cell culture especially well with oxygen and with nutrients. To support the mixing, mixing elements can be provided in the supply chamber, for example in the form of surface parts placed on the boundary walls of the supply chamber or in the form of mixing beads. An air bubble also contributes to mixing the nutrient medium. An air bubble can be present both in the supply chamber and in the cell culture chamber.

The supply module 3 is equipped with a tubular pressure finger 11 preferably made of silicone. This pressure finger extends starting from the face of the supply module 3 which is turned away from production module 2, close to parallel to its longitudinal axis into the inside of the supply module 3. The longitudinal axis of pressure finger 11 does not run along the longitudinal axis of the supply module, which represents the axis of rotation for culture vessel 1, but near it.

Figure 2:
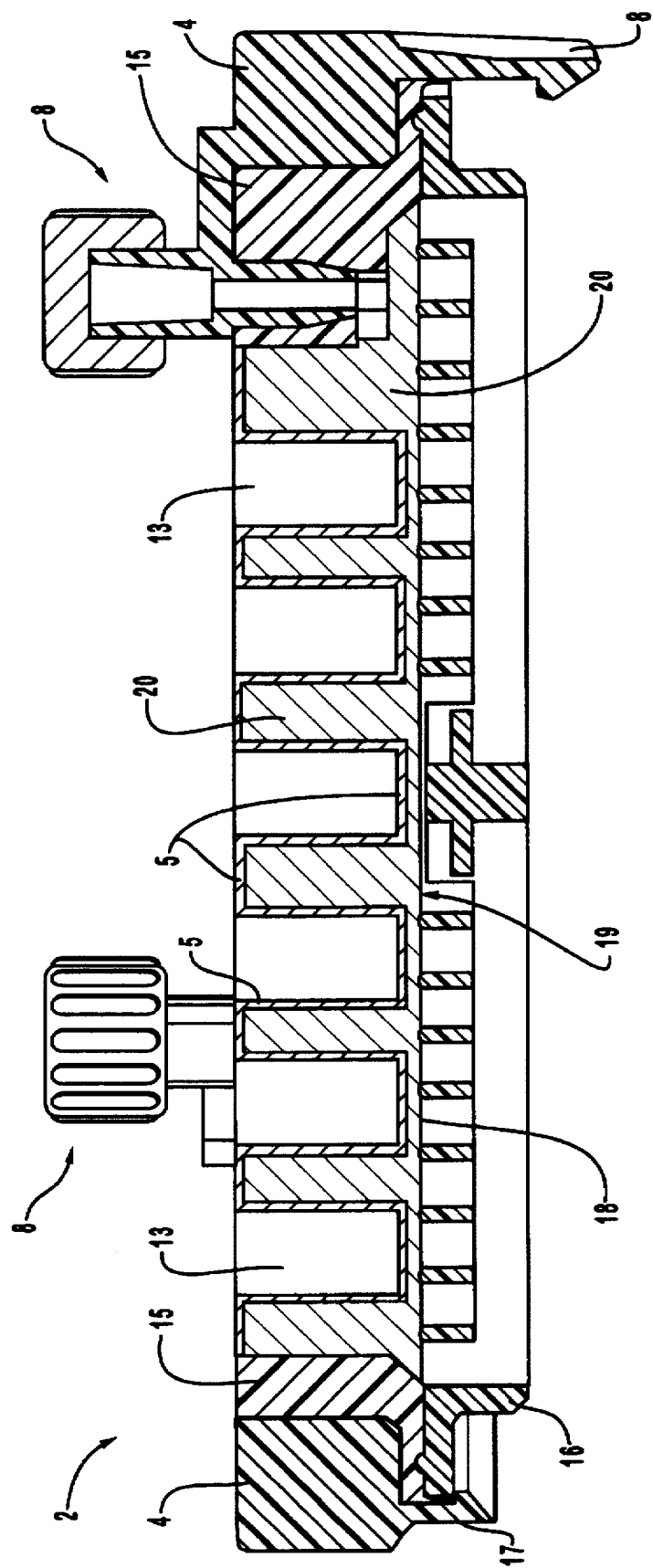
FIG. 2 a section through a cell culture chamber with a carrier placed in it.

The gas exchange membrane 5 of the preferred embodiment as depicted in FIG. 1 is provided with a plurality of inward-projecting nipples 13 which are circular in cross-section and extend into the production module 2, and which are open to the outside, as can be seen more clearly in the transverse section in FIG. 2.

In the preferred embodiment, the gases necessary for the gas supply are furnished to the cell culture chamber directly across the gas exchange membrane 5 from the surrounding atmosphere, and the gaseous metabolic products are removed directly from the cell culture chamber across the gas exchange membrane 5. Thus gases can be exchanged quickly and their exchange can be adjusted directly by the appropriate adjustment of the atmosphere surrounding the cell culture chamber and the pressure outside the cell culture chamber.

It has been proven advantageous to select the total surface area, the material, and the thickness of the gas exchange membrane 5 to supply oxygen in accordance with the oxygen demands of the desired high density cell cultures. Suitable gas exchange membrane 5 geometries and gas permeabilities can be determined by a few experiments. Suitable materials display a permeability coefficient for oxygen of at least $1 \times 10^{19}$ m²/sxPa, and it is more advantageous if it is at least $5 \times 10^{19}$ m²/sxPa. Silicone rubber and micro-porous materials which are or have been made hydrophobic, such as polytetrafluoroethylene, have proved to be especially well-suited materials for the gas exchange membrane 5. In order to ensure adequate oxygen supply, gas exchange membranes are preferred which are as thin as possible. Membranes with a thickness between 0.1 mm and 1 mm have proven themselves. Preferably, the gas exchange membrane 5 is about 0.2 mm thick.

In FIG. 2, the edge area 15 of the gas exchange membrane 5 is preferably thickened. In the edge area 15, the gas exchange membrane 5 is pinched between the support mesh 16 and the circular ring 4. For this purpose the circular ring 4 is provided with hooks 17 distributed uniformly around its circumference that catch over the edge of the support mesh 16. The support mesh 16 serves as a mechanical protection and as a support for the thin dialysis membrane 18, whose edge rests on the edge area 15 of the gas exchange membrane 5 and which is likewise pinched between the support mesh 16 and the circular ring 4.

In FIG. 2, the cell culture chamber is provided with a carrier for the cells to be cultivated which is in the form of a matte 19. The matte 19 is made of a three-dimensional network of fibers 20 which are matted together, and completely fills the cell culture chamber inside the production module 2.

In alternative implementations the fibers 20 can also be warp knitted, weft knitted, or woven. It is important in such implementations of the carrier that the matte 19 display a mechanical stability which allows openings to be punched out or cut out that correspond to the nipples 13 which extend into the production module 2. The thickness of the matte ideally corresponds approximately with the height of the production module 2 into which it is inserted so that it is easily removable. The fibers 20 preferably consist of polyhydroxybutyric acid, which is easily broken down in the human body. The nutrients for the cells growing on the matte 19 during cell cultivation are provided in the supply module next to the production module (not shown in FIG. 2). After completion of cell cultivation, the fibers 20 of the matte 19 have been coated with the cultivated cells. At this point the matte 19 can be removed from the cell culture vessel 1 and used directly, for example for a skin graft.

The cell culture vessel of the present invention features a carrier placed in a closable cell culture chamber. Any three-dimensional body on which cells can multiply is suitable as a carrier. Several individual carrier bodies can be provided, for example chips, granular powder, or beads. Such carriers can be kept in suspension by moving the cell culture chamber. Cultivation in suspension allows especially good supply of the cells adhering to the carrier body with oxygen and nutrients. The specific gravity of the carrier body can be selected in such a way that they float in the nutrient solution. This facilitates the stabilization of the suspension.

The carrier can also consist of a three-dimensional connected network. It is important that the geometry of the carrier allow the cells adhering to it to be adequately supplied with nutrients and oxygen by rinsing with a nutrient solution containing nutrients and oxygen, without contamination. It has proven especially worthwhile to use a three-dimensional network of fibers or fiber fragments 20. Such a network is distinguished by a large surface-to-volume ratio and allows the cultivation of high cell densities. The surface of the network can be structured or chemically modified in such a way to promote the adhesion of the cells to be cultivated. The fibers 20 can be either solid or hollow. If the fibers 20 are hollow an additional surface is available for the cells. The network can be inserted into the cell culture chamber, for example in the form of a matte 19 which is cut to the size which fits. It can also be produced directly in the cell culture chamber, for example, by spinning fibers in the cell culture chamber.

Especially worthwhile is a network having a mechanical stability which allows it to be injection molded out of a thermoplastic during the manufacture of the cell culture chamber. A carrier has also proven itself especially good which consists of a filter material or of a membrane material. It is good to modify the surface of the network in such a way that the cells adhere especially easily and multiply very quickly. This can be effected by a suitable surface structure as well as by a coating, for example, with collagen.

An implementation of the device in which the carrier is made in the form of a three-dimensional, porous network adjacent to the gas exchange membrane 5 has proved especially worthwhile. In this implementation the cells adhering to the carrier are especially well supplied with oxygen. The network can be in the form of a matte 19. The matte 19 can consist of one piece or can be assembled from several individual pieces, for example from hexagonal pieces.

One form of embodiment of the culture vessel is preferred in which the carrier is provided in the form of a "double layer" of two layers placed plane-parallel to one another. The layers preferrably consist of fibrous polyhydroxybutyric acid, a material which can be broken down biologically. The pore width of the layers is adjusted to be substantially smaller than the average cell size of human fibroblasts. On their faces the layers are welded together to form a hollow space. Later, the weld points which are thermally pre-loaded in this way dissolve quickly by hydrolysis and thus the layers easily separate from one another. Adding human fibroblasts forms a corresponding monolayer on the surface of the carrier which is turned away from the hollow space. This monolayer serves as a base for the growth of further cells, such as human keratinocytes. By successively adding corresponding cell cultures in this way the structure of human skin can be artificially copied on the carrier. After the cultivation is finished the double layer is separated by dissolving the weld points which can be hydrolyzed easily. The individual layers can then be used as skin grafts.

Another embodiment of the carrier which has proven itself in practice is in the form of a component formed from at least two porous layers in which each pair of layers lies opposite the other, especially with respect to the manufacture of skin grafts. The layers are separable from one another and their face sides lie on each other. The cells adhere first of all to the free surface. The step-wise buildup of various cell types on this surface can then, for example, artificially copy the cyto-architecture of the skin, while the opposite site of the layer remains free of cells. In order to avoid altogether any cell population on the opposite face sides, an implementation of the double layer is advantageous in which the layers lie close together or enclose a hollow space, the porosity of the layers being adjusted in such a way that the cells to be cultivated do not get between the layers or into the hollow space. Alternatively or additionally the opposite surfaces of the layers can be made hydrophobic. For this purpose the layer can be made hydrophobic by a coating, for example with polypropylene, or a separating formed fabric can be provided which covers the layer. This will hinder cell growth on these layers.

It has been shown that a cell culture vessel according to the invention, especially when the carrier is in the form of a three-dimensional porous network, is especially well suited for the manufacture of skin grafts after the cultivation of skin cells.

A form of embodiment of the culture vessel has proven to be especially valuable in practice wherein the cells to be cultivated are poured in a fluid medium into the production module 2, which has a volume of approximately 35 ml. A carrier in the form of a flexible matte 19 is inserted into the production module 2. The matte 19 is formed from a three-dimensional network of fibers 20 connected with one another. The substantially larger supply module 3 (approximately 600 ml) is filled to ⅔ with the nutrient medium. Neither the cells nor the high-molecular products released by the cells can pass through the semipermeable dialysis membrane 18. By contrast, nutrients, vitamins, ions, and gases ($O_2$, $CO_2$) which are physically dissolved in the medium can pass almost unhindered from the supply module 3 into the production module 2, and, because of the approximately 10-fold excess of supply medium, can supply the cells with the substances necessary for cultivation over a long period of time (depending on the cell density). Simultaneously the acidic, toxic, and other metabolites released by the cells can leave the production module 2 across the dialysis membrane 18 and can be taken up and neutralized in the substantially larger volume of the supply module 3. This allows higher cell densities and high thicknesses of cell products to be attained.

It has proven especially advantageous in practice to rotate the culture vessel 1 around its longitudinal axis. This ensures an optimal exchange of substances on the dialysis membrane 18 and on the gas exchange membrane 5. The nutrient solution reaches every fiber 20 through the network-like, porous structure of the matte 19 as the cells are rinsed continuously with nutrient medium.

The pressure finger 11, which projects into the supply module 3 and is preferrably covered with a thin silicone membrane, also makes sure that exchange of substances is optimal on dialysis membrane 18 and gas exchange membrane 5. This pressure finger absorbs pressure fluctuations arising during cell cultivation and simultaneously makes possible the exchange of gases between the supply module 3 and the incubator atmosphere. Its eccentric placement, outside the axis of rotation also serves to improve the mixing of the nutrient medium. The length and diameter of the pressure finger 11 are adapted to the maximum expected pressure fluctuations. When there is overpressure inside the supply module 3 the pressure finger 11 is pressed together. This prevents the dialysis membrane 18 and the gas exchange membrane 5 from bulging and thus prevents a change in the volume of production module 2 and the mixture conditions. Thus the pressure finger 11 ensures a reproducible cell culture.

Figure 3:
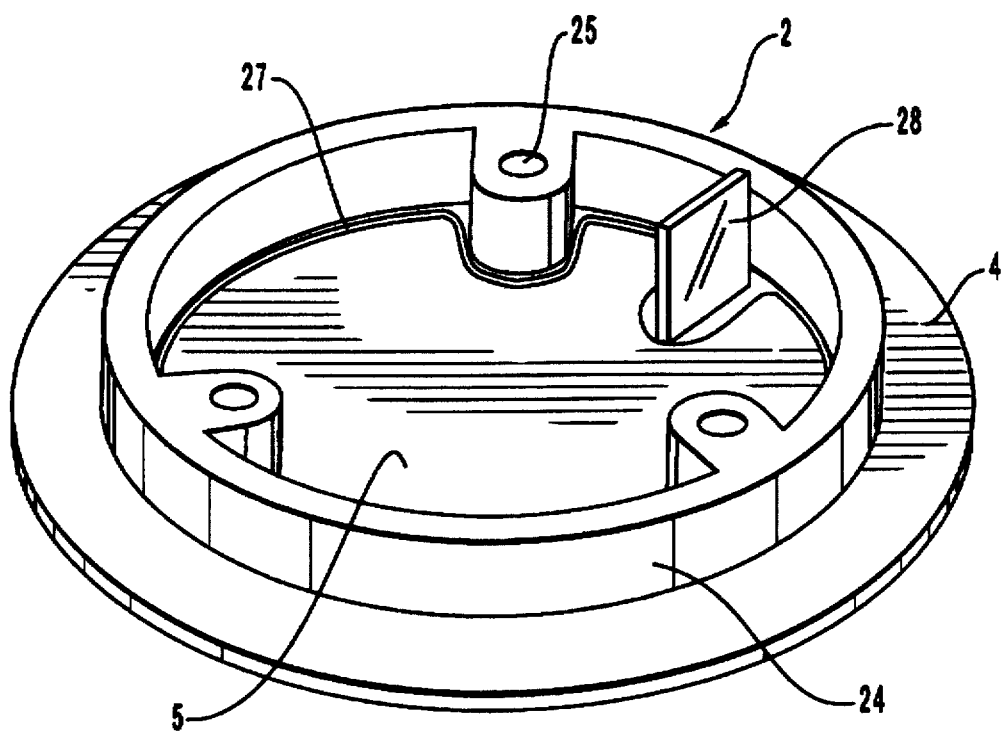
FIG. 3 a schematic representation of the top view of a cell culture chamber with a detachable gas exchange membrane.
Figure 4:
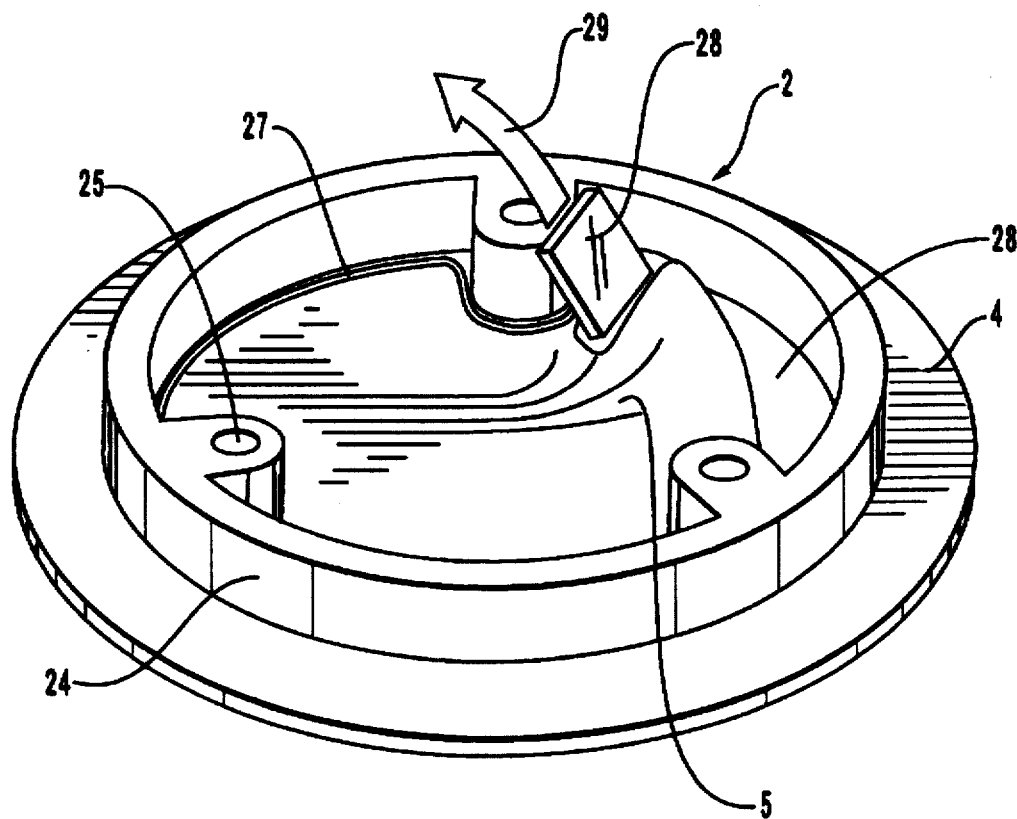
FIG. 4 the cell culture chamber according to FIG. 3 with a partially removed gas exchange membrane.

The implementation of the production module 2 presented in FIGS. 3 and 4 is especially suitable for the cultivation according to the invention using a carrier in the form of a matte formed of several individual layers, the individual layers being easily separable from one another and individually removable from the cell culture chamber after cultivation.

FIGS. 3 and 4 show the production module 2 with a stable circular ring 4, which is provided on its inner edge with a lip 24, in which are formed the connection openings 25 for the Luer lock connections. To facilitate the removal of the individual layers from the cell culture chamber (see FIG. 4), the gas exchange membrane 5 serving for the exchange of gases is provided with a tear-away edge 27 running around the circumference in the area of the lip 24 and with a pull-off tab 28.

FIG. 4 shows the removal of the gas exchange membrane 5. For this purpose the pull-off tab 28 is simply pulled in the direction indicated by the direction arrow 29. The gas exchange membrane 5 tears along the tear-away edge 27 and can be completely removed. The inside of the cell culture chamber is then freely accessible and the individual layers covered with the cell culture can be then be removed.

In the preferred embodiment of the cell culture vessel the gas exchange membrane is made so that it can be separated from the cell culture chamber. This makes it possible to open the cell culture chamber by removing the gas exchange membrane 5 and to remove the carrier which is covered with cells after the end of cell cultivation. The formation of the tear-away edge 27 can be implemented by making the gas exchange membrane 5 with a thicker area running around its edge which tapers off in the direction of the tear-away edge 27 and which corresponds with a thicker area made in the same way on the opposite side of the tear-away edge 27.

Figure 5:
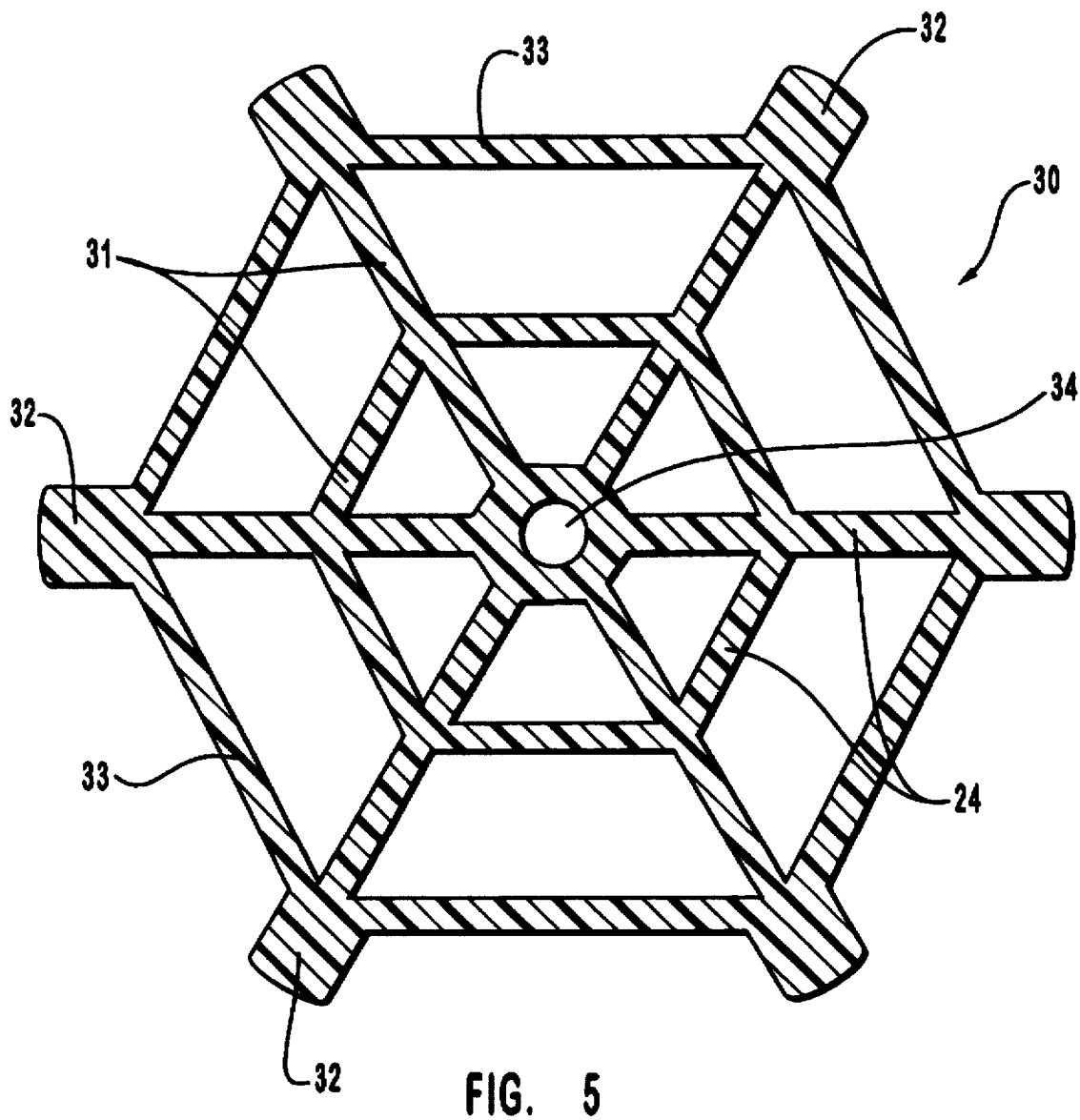
FIG. 5 a schematic representation of a support mesh to hold a carrier.

FIG. 5 illustrates the support mesh 30 which is especially suitable for the cultivation of cells on carriers in the form of flexible membranes that have inadequate mechanical stability. Such a support mesh allows the carrier itself to have very thin walls because the mechanical stability is taken over by the support mesh. The preferred embodiment of the support mesh 30 consists of stays 31 connected with one another preferably made of a weldable plastic, which form a regular hexagon. For cell cultivation the membranes are welded to the support mesh 30. For this purpose the support mesh 30 has a total of six weld areas 32 which are arranged in a regular hexagon around the support mesh 30. The hexagon formed by the weld areas is thus outside the outer-most hexagonal stay 33 of the support mesh 30. The membranes to be held to support mesh 30 likewise have a hexagonal structure and their size corresponds approximately to that of the support mesh 30. Just as was the case with support mesh 30, the membrane is provided with welding surfaces which are outside of its hexagonal surface and whose geometric arrangement and size corresponds to welding areas 32. Several of these support meshes 30 are stacked inside the production module (not shown). In order to facilitate coaxial stacking every support mesh 30 is provided with a central supporting borehole 34. The distance between neighboring support meshes 30 is preferably in the range of a millimeter. The stacking of the support meshes in the production module allows cell cultivation on thin-walled membranes in the narrowest space without the membranes touching or the cell cultures of neighboring membranes growing together.

In the preferred embodiment, it is advantageous if the support mesh 30 is in the form of a flat support piece on which mounting points are provided for the carrier. The holes in the mesh structure of the support piece ensure that the cells growing on the carrier are adequately supplied. For flat carriers, which are in the form of a regular hexagon (apart from the supporting surfaces corresponding with the mounting points), a support piece has proven worthwhile in which the mounting points are placed outside the hexagonal surface of the carrier. The support surfaces of the carrier are likewise outside the hexagonal surface and they correspond with the mounting points. The carrier is attached to the support piece, for example, by welding. However the carrier normally becomes unusable for cell cultivation at weld points 32. Therefore the support surfaces are chosen as small as possible. The fact that the carrier is in the shape of a regular hexagon makes it possible to fill a large surface without a gap by placing several carriers together. The support surfaces by which the carrier is fastened to the support piece lie outside the hexagonal surface and are cut off. Naturally a large surface without a gap can also be produced by placing carriers together having a triangular or rectangular shape. The hexagonal shape has the further advantage that it better fills up a round cross-section, for example of a cylindrical bottle.

As a result of the preferred embodiment illustrated in FIG. 5, a carrier can be built of several layers that in turn can be separated from one another. Such a carrier makes it possible, after the cell cultivation has finished, to remove individual layers each of which is coated with the cell culture. These layers can be coated with skin cells and can be used, for example, as a skin replacement during transplantations. A special advantage of such a carrier also consists of the fact that a single cell culture can produce a large skin replacement surface simultaneously. In this connection a carrier which consists of a material which can be broken down biologically has proven especially worthwhile.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed by United States Letters Patent is:

1. A cell culture vessel comprising:

a cell culture chamber for receiving a cell culture;

a supply chamber for receiving a nutrient medium;

a dialysis membrane interposed between the cell culture chamber and the supply chamber whereby nutrients are separated from the cell culture chamber but may be transported from the supply chamber through the dialysis membrane into the cell culture chamber and whereby metabolic waste products may be transported out of the cell culture chamber through the dialysis membrane and into the supply chamber;

a gas exchange membrane interposed between the cell culture chamber and a source of oxygen which is permeable to gas, wherein the gas exchange membrane is detachable from the cell culture chamber;

a removal device comprising a break-away edge running around the edge of said gas exchange membrane;

a three-dimensional carrier for the cell; and a support piece for said carrier.

2. A cell culture vessel in accordance with claim 1, wherein the carrier consists of filter or membrane material.

3. A cell culture vessel in accordance with claim 2, wherein the carrier includes a three-dimensional network made of fibers or of fiber fragments.

4. A cell culture vessel in accordance with claim 3, wherein the carrier is made in the form of a three-dimensional porous network adjacent to the gas exchange membrane.

5. A cell culture vessel in accordance with claim 4, wherein the carrier is formed of at least two porous layers, each pair of the layers lying opposite one another.

6. A cell culture vessel in accordance with claim 5, wherein the carrier several layers are detachable from one another.

7. A cell culture vessel in accordance with claim 6, wherein by the layers lie tight together or enclosed a hollow space.

8. A cell culture vessel in accordance with claim 7, wherein by the porosity of the layers is adjusted in such a way that the cells to be cultivated cannot get between the layers or into the hollow space.

9. A cell culture vessel in accordance with claim 8, wherein the opposite surfaces of the layers are made hydrophobic.

10. A cell culture vessel in accordance with claim 2, characterized by the fact that the carrier has a coating which promotes cell growth.

11. A cell culture vessel in accordance with claim 10, wherein the surface of the carrier is chemically modified to promote cell growth.

12. A cell culture vessel in accordance with claim 2, wherein the carrier is made in the form of a stable matte which can be extruded with plastic.

13. A cell culture vessel in accordance with claim 12, wherein the carrier is placed into the cell culture chamber so that it can be detached.

14. A cell culture vessel in accordance with claim 13, wherein the carrier consists of a material which can be broken down in the human body.

15. A cell culture vessel in accordance with claim 14, wherein the support piece is made as a flat support screen, on which mounting points are provided for the carrier.

16. A cell culture vessel in accordance with claim 15, wherein the carrier is flat and, except for the supporting surfaces corresponding to the mounting points, in the form of a regular hexagon, and that the supporting surfaces and the corresponding mounting points are placed outside the hexagonal surface of the carrier.

* * * * *

UNITED STATES PATENT AND TRADEMARK OFFICE
CERTIFICATE OF CORRECTION

PATENT NO. : 5,702,945
DATED : December 30, 1997
INVENTOR(S) : Hans-Otto Nagels; Dieter Schröder; Eckart Kopowski It is certified that error appears in the above-identified patent and that said Letters Patent is hereby corrected as shown below:

Title Page, Other Publications, after "In" change "Vivo" to --Vitro--

Page 2, Other Publications, Left Column, line 9, after "Alternatives" change "an" to --and--

Col. 7, line 30, after "to" change "2/3with" to --2/3 with--

Col. 10, line 24, after "enclosed" insert --in--

Signed and Sealed this

Fourteenth Day of July, 1998

*Attest:*

BRUCE LEHMAN

*Attesting Officer*  *Commissioner of Patents and Trademarks*